US00PP19914P2

(12) United States Plant Patent
Bradford

(10) Patent No.: US PP19,914 P2
(45) Date of Patent: Apr. 14, 2009

(54) NECTARINE TREE NAMED 'CANDYSWEET X'

(50) Latin Name: *Prunus persica*
Varietal Denomination: CANDYSWEET X

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 0 days.

(21) Appl. No.: 12/003,393

(22) Filed: Dec. 26, 2007

(51) Int. Cl.
*A01H 5/00* (2006.01)

(52) U.S. Cl. ..... Plt./190
(58) Field of Classification Search ..... Plt./190
See application file for complete search history.

(56) References Cited

U.S. PATENT DOCUMENTS

| | | | |
|---|---|---|---|
| PP7,918 | P | 7/1992 | Bradford |
| PP10,924 | P | 5/1999 | Bradford |
| PP16,585 | P2 | 5/2006 | Bradford |

*Primary Examiner*—Annette H Para
*Assistant Examiner*—June Hwu

(57) ABSTRACT

The present invention relates to a new and distinct variety of nectarine tree, *Prunus persica,* broadly characterized by a medium size, vigorous, hardy, self-fertile, productive and regular bearing tree. The variety blooms during the mid season and requires about 550 chilling hours. The fruit matures under the ecological conditions described in late June, with first picking on Jun. 18, 2007. The fruit is uniformly large in size, sub-acidic and sweet in flavor, globose in shape, clingstone in type, firm and melting in texture, yellow in flesh color, and almost full red in skin color.

1 Drawing Sheet

Botanical classification: *Prunus persica.*
Variety denomination: 'CANDYSWEET X'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'Candysweet X'.

The present variety was hybridized by me in 1996 as a first generation cross using 'Ruby Diamond' (U.S. Plant Pat. No. 7,918) nectarine as the selected seed parent and 'Candy White' (U.S. Plant Pat. No. 10,924) nectarine as the selected pollen parent. The fruit of this cross was gathered in the summer of 1996, and the seeds were removed, cracked, stratified, germinated, and grown as seedlings on their own root in my greenhouse. Upon reaching dormancy the group of seedlings was transplanted to a cultivated area of my experimental orchard located near Le Grand, Calif., in Merced County (San Joaquin Valley). During the fruit evaluation season of 2000 I selected the present variety as a single tree from the group of seedlings described above. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its seed parent, 'Ruby Diamond' nectarine by producing nectarines that are firm, yellow in flesh color, and nearly full red in skin color, but is quite distinguished therefrom by producing fruit that is clingstone instead of freestone, sub-acidic in flavor instead of acidic, and that matures about two weeks earlier.

The present variety is similar to its pollen parent, 'Candy White' nectarine by producing nectarines that are firm, nearly full red in skin color, sub-acidic in flavor, and that mature in late June, but is quite distinguished therefrom by producing fruit that is larger in size, clingstone instead of freestone, and yellow instead of white in flesh color.

The present variety is more similar to 'Sugarine I' (U.S. Plant Pat. No. 16,585) nectarine by producing fruit that is firm, yellow in flesh color, nearly full red in skin color, and sub-acidic in flavor, but is distinguished therefrom by having reniform instead of globose glands and by producing fruit that is somewhat sweeter, that has a little more freckling on the skin, and that matures about two weeks earlier.

SUMMARY OF VARIETY

In summary, the present variety is characterized by a medium size, vigorous, hardy, self-fertile, productive and regular bearing tree. The variety blooms during the mid season and requires about 550 chilling hours. The fruit matures under the ecological conditions described in late June, with first picking on Jun. 18, 2007. The fruit is uniformly large in size, sub-acidic and sweet in flavor, globose in shape, clingstone in type, firm and melting in texture, yellow in flesh color, and almost full red in skin color.

DRAWING

The accompanying photograph consists of four whole fruits positioned to display the characteristics of the skin color and form, one sliced fruit to reveal the flesh and stone, three insets to reveal buds and a blossom, characteristic leaves, and a typical tip shoot.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 26, 2007, on the original tree during its eleventh growing season. The blossom and flower descriptions were made the previous blooming season. All major color code designations are by reference to the Inter-Society Color Council, National Bureau of Standards. Common color names are also used occasionally.

Parentage

Seed parent: 'Ruby Diamond' (U.S. Plant Pat. No. 7,918) nectarine.

Pollen parent: 'Candy White' (U.S. Plant Pat. No. 10,924) nectarine.

Tree

Size: Medium, reaching and maintaining a height of 9' [2.74 m.] and a spread of 10' [3.05 m.] after eleven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase type.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Approximate chilling requirement: 550 hours.

Trunk:

*Size.*—Medium, reaching a maximum diameter of 5¼" [133 mm.] after the eleventh growing season.

*Texture.*—Shaggy.

*Bark color.*—A Grayish brown [61. gy.Br] and Grayish yellowish brown [80. gy.yBr] variegation with Deep yellowish brown [75. deep yBr] crevices present.

*Lenticels.*—Approximate Number Per Square Inch: 6. Color: Moderate orange yellow [71. m.OY]. Average Size: ¼" [6.4 mm.]. Shape: Eye-shaped, elongated.

Branches:

*Size.*—Diameter of limb is 2¾" [70 mm.] measured 12" above the crotch, 1¾" [45 mm.] measured 12" above the first fork.

*Texture.*—Smooth on first and second year wood, increasing roughness with age.

*Color.*—1st Year Wood Topside: Grayish red [19. gy.R]. 1st Year Wood Underside: Brilliant yellow green [116. brill.YG]. Older Wood: Moderate brown [58. m.Br].

*Lenticels.*—Number Per Square Inch: More than 60 on second year wood. Color: Deep orange yellow [69. deep OY]. Average size: 1/32" [0.8 mm.] on second year wood. Shape: Rectangular, elongated. Leaves:

*Size.*—Medium. Average Length: 5 15/16" [151 mm.]. Average Width: 1⅝" [41 mm.].

*Arrangement.*—Alternate.

*Thickness.*—Medium.

*Form.*—Elliptical.

*Apex.*—Acuminate.

*Base.*—Acute, with an average base angle of 75 degrees.

*Surface.*—Smooth.

*Color.*—Dorsal Surface: Moderate olive green [125. m.OlG]. Ventral Surface: Moderate yellow green [120. m.YG].

*Margin.*—Finely serrate.

*Venation.*—Pinnately net veined.

*Vein color.*—Light yellow green [119. l.YG].

*Petiole.*—Average Length: ¼" [6.4 mm.]. Average Thickness: 1/16 [1.6 mm.]. Color: Strong yellow green [117. s.YG].

*Stipules.*—Number: Usually 2 per leaf, up to 6 per growing tip. Average Length: ¼" [6.4 mm.]. Color: Strong yellow green [117. s.YG] becoming Deep reddish brown [41. deep rBr] with maturity.

*Glands.*—Number: 3 to 4 per leaf. Position: Alternately positioned on petiole. Size: Medium. Form: Reniform. Color: Brilliant yellow green [116. brill.YG] becoming Strong yellowish brown [74. s.yBr] with age.

*Leaf buds.*—Pointed, medium in size.

Flower buds:

*Hardiness.*—Hardy, with respect to central California winters.

*Diameter.*—Typically ⅜" [9.5 mm.] 1 week before bloom.

*Length.*—Typically ⅝" [15.9 mm.] 1 week before bloom.

*Form.*—Not appressed.

*Surface.*—Pubescent.

*Tip color.*—Light purplish pink [249. l.pPk].

Flowers: Perfect, complete, perigynous, usually a single pistil, typically thirty or more stamens, five sepal and petal locations alternately positioned.

*Type.*—Showy, large.

*Average flower diameter.*—2" [50.8 mm.].

*Number of petals.*—Mostly five, a few with extra petal fragments, a few double blossoms with ten petals.

*Petal shape.*—Circular to oval.

*Petal margin.*—Entire, wavy, occasional notches.

*Average petal diameter.*—13/16" [20.6 mm.].

*Average petal length.*—13/16" [20.6 mm.].

*Petal apex.*—Rounded.

*Petal base.*—Rounded to somewhat truncate.

*Petal color.*—Pale pink [7. p.Pk] toward the apex, Dark purplish pink [251. d.pPk] toward the base on both sides.

*Anther color.*—Moderate purplish red [258. m.pR] over a Light yellow [86. l.Y] center at bloom onset.

*Stigma color.*—Pale greenish yellow [104. p.gY].

*Sepal color.*—Dark purplish red [259. d.pR] on the outer surface.

*Sepal length.*—¼" [6.4 mm.].

*Sepal width.*—3/16" [4.8 mm.].

*Sepal apex.*—Rounded to elliptical to match the sepal length and width.

*Sepal margin.*—Fairly smooth.

*Average pistil length.*—11/16" [17.5 mm.].

*Average stamen length.*—9/16" [14.3 mm.].

*Fragrance.*—Moderate.
*Blooming period.*—Medium, with 'Spring Bright' (U.S. Plant Pat. No. 7,507) nectarine.
*Onset of bloom.*—One percent on Mar. 2, 2007.
*Date of full bloom.*—Mar. 10, 2007.
*Duration of bloom.*—One to two weeks, dependent on ambient temperature.
*Number per cluster.*—1 to 3 with single flowers most common.

FRUIT

*Maturity when described.*—Firm ripe, Jun. 26, 2007.
*Date of first picking.*—Jun. 18, 2007.
*Date of last picking.*—Jun. 28, 2007.
*Size.*—Uniform, medium.
*Average diameter axially.*—2¾" [69.9 mm.].
*Average diameter across suture plane.*—2⅞" [73.0 mm.].
*Average diameter across suture plane.*—2⅞" [73.0 mm.].
*Typical weight.*—8.1 ounces [230 grams].
Form: Globose, symmetrical.
*Longitudinal section form.*—Round to elliptical.
*Transverse section through diameter.*—Round.
Suture: Extends from the base, along the side and terminates just past the pistil point.
*Near the base.*—A shallow groove.
*Along the side.*—An inconspicuous line.
*Near the apex.*—A moderately sharp groove.
Ventral Surface: Rounded, lipped toward the apex.
Lips: Equal.
Cavity: Flaring, elongated in the suture plane, suture showing on one side, Brilliant orange yellow [67. brill.OY] stem markings typical.
*Depth.*—7/16" [11.1 mm.].
*Breadth.*—1½" [38.1 mm.].
Base: Rounded to slightly truncate.
Apex: Rounded, but cordate if viewed parallel to the suture.
Pistil Point: Oblique, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Non-astringent.
*Tendency to crack.*—Slight in wet season.
*Color.*—Very deep red [14. v.deep R] over a Strong red [12. s.R] background with Dark orange yellow [72. d.OY] freckling toward the apex.
Flesh:
*Color.*—Brilliant orange yellow [67. brill.OY] with the slightest amount of Moderate red [15. m.R] streaking next to the stone.
*Surface of pit cavity.*—Covered with Deep pink [3. deep Pk] broken fibers when twisted from the stone.
*Amygdalin.*—Scarce.
*Juice.*—Moderate, rich.
*Texture.*—Firm, crisp.
*Fibers.*—Abundant, fine, tender.
*Ripens.*—Slightly earlier at the apex.
*Flavor.*—Sub-acid and sweet, typically 20 brix.
*Aroma.*—Slight.
*Eating quality.*—Very good.

STONE

Type: Clingstone.
Form: Oval.
Hilum: Narrow, oblong.
Base: Straight, rounded.
Apex: Acute to acuminate, with an average tip angle of 70 degrees and a tip of length ⅛" [3.2 mm.].
Sides: Equal.
Surface: Irregularly furrowed near the apex, pitted toward the base.
Ridges: Jagged.
External color: Moderate brown [58. m.Br].
Pit wall color when cracked: Light brown [57. l.Br].
Cavity surface color: Strong brown [55. s.Br].
Average pit wall thickness: ¼" [6.4 mm.].
Average width: 1 1/16" [27.0 mm.].
Average length: 1 9/16" [39.7 mm.].
Average breadth: 13/16" [20.6 mm.].
Tendency to split: Slight.
Kernel:
*Form.*—Oval.
*Skin color.*—Brilliant yellow [83. brill.Y] when first removed.
*Pellicle color.*—Grayish yellowish brown [80. gy.yBr].
*Vein color.*—Grayish yellow [90. gy.Y].
*Taste.*—Sweet.
*Viable.*Yes.
*Average width.*—9/16" [14.3 mm.].
*Average length.*—¾" [19.1 mm.].
*Amygdalin.*—Scant.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is similar to 'Sugarine I' (U.S. Plant Pat. No. 16,585) nectarine by producing fruit that is firm, yellow in flesh color, nearly full red in skin color, and sub-acidic in flavor, but is distinguished therefrom by having reniform instead of globose glands and by producing fruit that is somewhat sweeter, that has a little more freckling on the skin, and that matures about two weeks earlier.

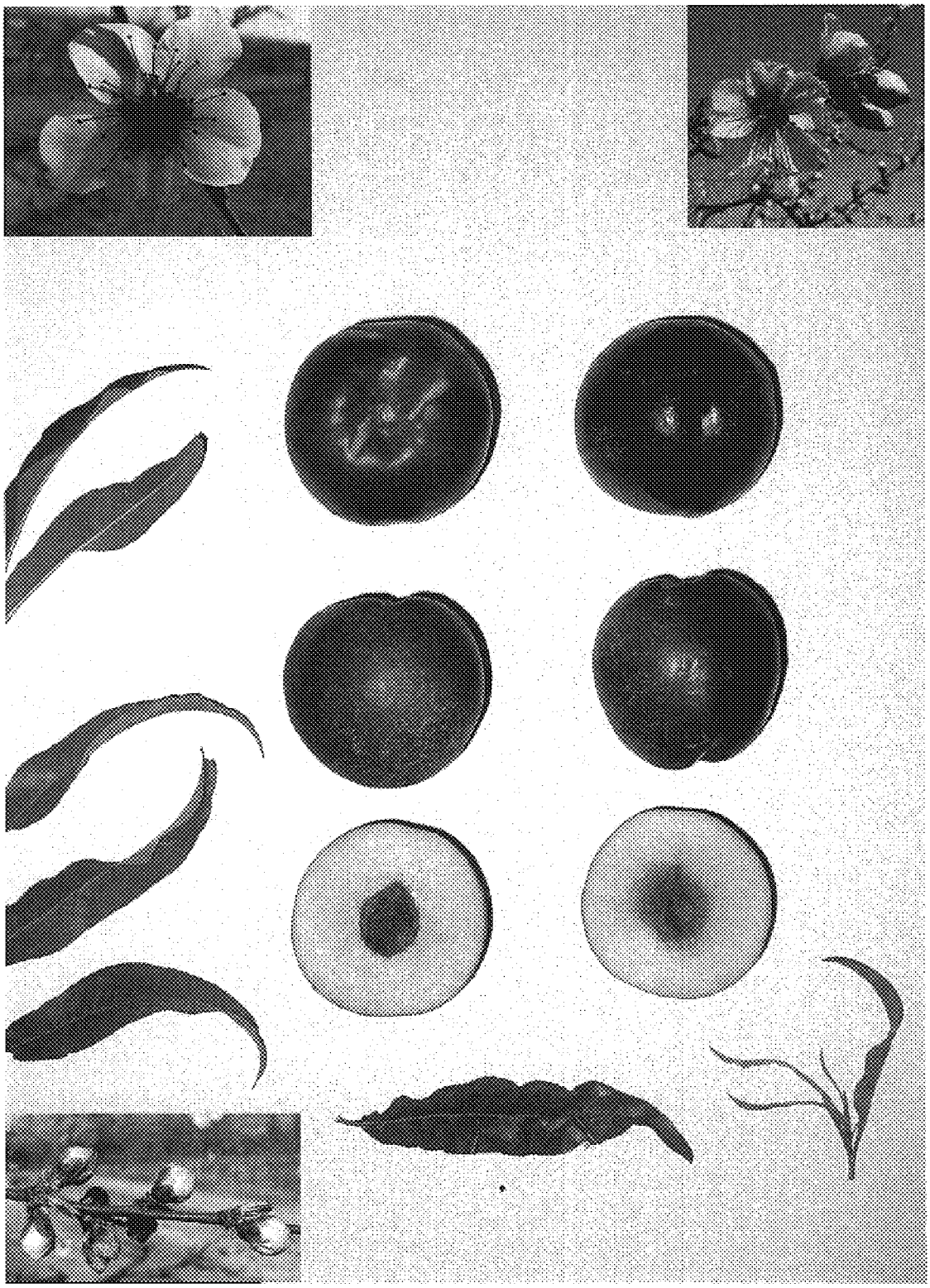

* * * * *